(12) United States Patent
Yamamoto et al.

(10) Patent No.: US 6,787,349 B1
(45) Date of Patent: Sep. 7, 2004

(54) BIOCHIP READER AND LABELING REAGENT

(75) Inventors: Kenji Yamamoto, Kanagawa (JP);
Mitsuhiro Tachibana, Kanagawa (JP);
Katsuya Mizuno, Kanagawa (JP)

(73) Assignee: Hitachi Software Engineering Co., Ltd., Kanagawa (JP)

( * ) Notice: Subject to any disclaimer, the term of this patent is extended or adjusted under 35 U.S.C. 154(b) by 361 days.

(21) Appl. No.: 09/889,747

(22) PCT Filed: Nov. 15, 2000

(86) PCT No.: PCT/JP00/08050
§ 371 (c)(1),
(2), (4) Date: Jul. 19, 2001

(87) PCT Pub. No.: WO01/38875
PCT Pub. Date: May 31, 2001

(30) Foreign Application Priority Data

Nov. 19, 1999 (JP) ............................................ 11/329945

(51) Int. Cl.$^7$ .......................... C12M 1/00; G01N 37/00
(52) U.S. Cl. ................................ 435/287.2; 435/287.1; 436/56
(58) Field of Search .......................... 360/97.01; 435/6, 435/285.1, 285.2, 288.7; 324/201, 204; 436/56

(56) References Cited

U.S. PATENT DOCUMENTS 5,656,429 A * 8/1997 Adelman ........................ 435/6
6,037,167 A * 3/2000 Adelman et al. ........ 435/285.1

FOREIGN PATENT DOCUMENTS

| JP | 11094747 | 4/1999 |
|----|----------|--------|
| WO | WO 89/09282 | 3/1989 |
| WO | WO 90/06042 | 11/1989 |
| WO | WO 90/11369 | 3/1990 |
| WO | WO 92/01812 | 7/1991 |
| WO | WO 92/17609 | 4/1992 |
| WO | WO 93/08305 | 10/1992 |
| WO | WO 93/20232 | 4/1993 |
| WO | WO 96/10644 | 9/1995 |

* cited by examiner

*Primary Examiner*—A. J. Heinz
(74) *Attorney, Agent, or Firm*—Reed Smith LLP; Stanley P. Fisher, Esq.; Juan Carlos A. Marquez, Esq.

(57) ABSTRACT

The present invention provides a high-sensitive, inexpensive biochip reader for reading a biochip as compared to a fluorescence method. The biochip reader is provided with an X-Y stage (3) for mounting a biochip (6) and scanning the biochip (6) in a two-dimensional manner, a controller (4) for the X-Y stage, a magnetic sensor (1) for reading the magnetic field strength, an ohmmeter (2), and a computer (5) for signal processing. As a result, a high-performance, inexpensive biochip reader can be provided without using an expensive laser or an expensive optical system, by employing a magnetic sensor and a disk driving mechanism generally used in a hard disk drive and the like.

9 Claims, 6 Drawing Sheets

BIOCHIP READER AND LABELING REAGENT

This application is a 371 of PCT/JP00/08050 filed Nov. 15, 2000 and claims priority to Japanese Application Serial No. 329945/1999, filed Nov. 19, 1999.

FIELD OF THE INVENTION

The present invention relates to a biochip reader for detecting a binding spot on a biochip having an array of spots that bind with specific biological substances, and to a labeling reagent desirable for producing the biochip to be read with such a biochip reader.

BACKGROUND ART

Conventionally, in order to identify and/or fractionate biological molecules, particularly to detect DNA of interest or detect the presence of gene DNA, method of hybridization is often employed where probes such as nucleic acids or proteins having known sequences are used to hybridize to a sample nucleic acid or a sample protein. A biochip is provided with spots of probes (e.g., nucleic acids, proteins, etc.) integrated thereon at a high density, and is used to efficiently detect DNA of interest or detect the presence of gene DNA.

FIG. 6 is a schematic view showing an exemplary structure of a conventional biochip reader. Currently, a fluorescence reading technique is generally employed as a technique for detecting the hybridized spots. The sample nucleic acid or the sample protein is labeled with a fluorescent substance, and then subjected to hybridization to the probes spotted on the biochip. An excitation beam 16 from a laser 15 as an excitation light source is reflected off a dichroic mirror 17 and passed through a condenser lens 18 to radiate the spots hybridized with the sample. The fluorescent substance which labels the sample is excited by this excitation light. The emitted fluorescence is converged by the condenser lens 18, passes through the dichroic mirror 17 and an optical interference filter 19 which selectively transmits the fluorescence component to cut optical components causing noise, and is guided to a photomultiplier 20. The photomultiplier 20 is a point sensor, so a controller 4 make the photomultiplier 20 to scan the sample in X- and Y-directions and a computer 5 acquires the scanned data as an image from the photomultiplier 20.

According to such a conventional fluorescence technique, however, an expensive laser 15 and an expensive optical system are required for the reading process, thereby increasing the cost of the device. Furthermore, the fluorescence intensity from the fluorescent substance is weak, and the wavelength of the fluorescence is not sufficiently far from that of the excitation light to completely remove the excitation light with the optical interference filter 19 in front of the photomultiplier 20. As a result, detection with the fluorescence label does not give highly-sensitive detection.

In view of the above-described problem, the present invention has an objective of providing a biochip reader which is more sensitive and inexpensive than- the fluorescence technique, and providing a labeling reagent desirable for producing a biochip that is read by such a biochip reader.

DISCLOSURE OF THE INVENTION

A biochip reader of the present invention comprises: a magnetic sensor for reading the strength of the magnetic field on a plane; and a scanning unit for driving the magnetic sensor and the biochip so that the magnetic sensor scans the biochip relatively in a two-dimensional manner.

The scanning unit rotates the biochip and drives the magnetic sensor in a uniaxial direction perpendicular to the rotating direction, thereby incorporating a disk-reading mechanism of a general hard disk drive.

Furthermore, a labeling reagent of the present invention comprises a ferromagnetic substance for labeling a biological substance.

BEST MODES FOR CARRYING OUT THE INVENTION

Hereinafter, preferable embodiments of the present invention will be described with reference to the accompanying drawings.

Figure 1:
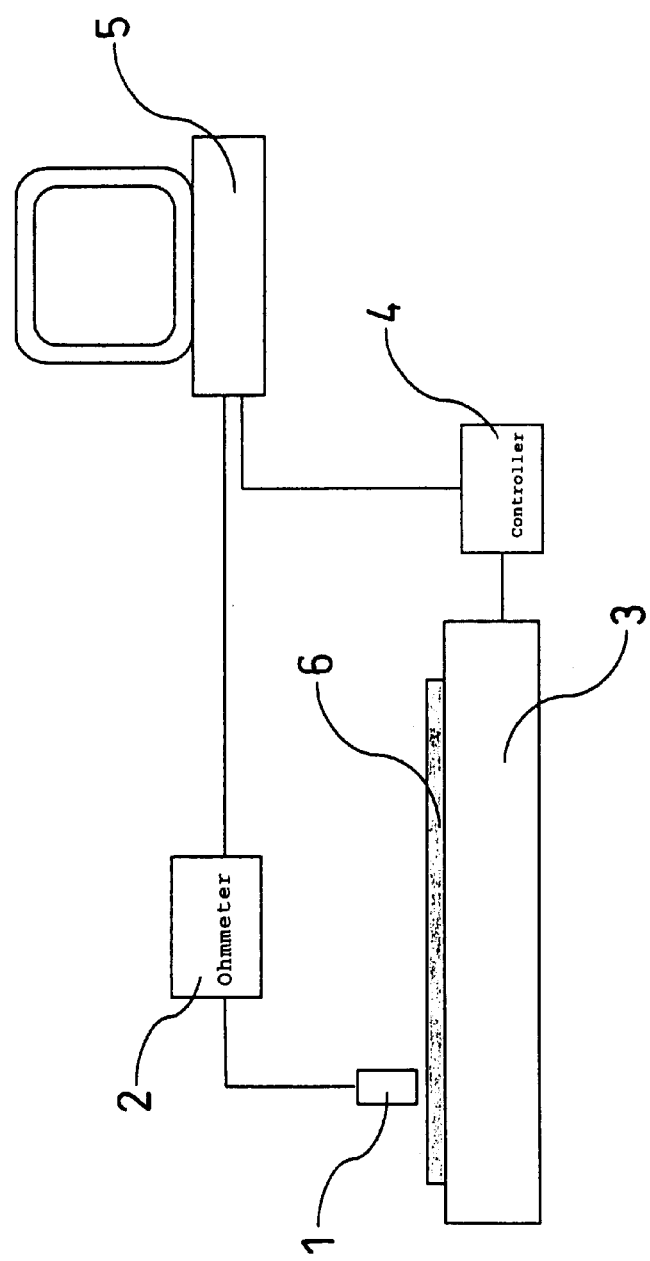
FIG. 1 is a view showing a structure of a biochip reader according to one embodiment of the invention.

FIG. 1 is a view showing a structure of a biochip reader according to one embodiment of the present invention. The biochip reader of this embodiment is provided with an X-Y stage 3 for mounting a biochip 6 and scanning the biochip 6 in a two-dimensional manner, a controller 4 for the X-Y stage 3, a magnetic sensor 1 for reading the magnetic field strength, an ohmmeter 2, and a computer 5 for signal processing.

As the magnetic sensor 1 for reading the magnetic field intensity, a GMR (Giant Magneto Resistance) element which is often used as a magnetic head of a high-density hard disk drive is used. The GMR element can detect the change of the magnetic field as a change of the electric resistance. Thus, the strength of the magnetic field can be signalized via the ohmmeter 2 and inputed into the signal-processing computer 5.

Figure 2:
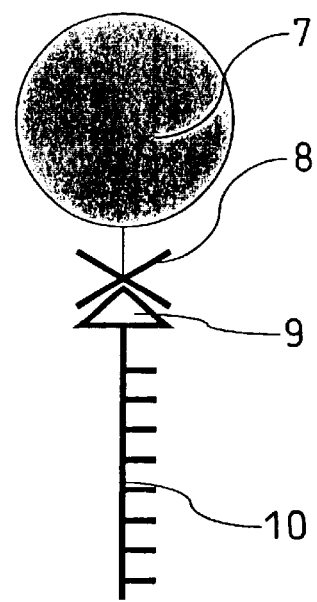
FIG. 2 is a view illustrating a method for labeling a sample.

FIG. 2 is a view for illustrating a method for labeling a sample. In the present embodiment, DNA is used as a biological sample, which is labeled with a substance that magnetizes the DNA, a ferromagnetic substance. According to the present embodiment, a magnetic bead 7 is used which is polystyrene encapsulating a ferromagnetic iron oxide particulate generally used in a magnetic recording medium (e.g., hard disk). The polystyrene encapsulating the magnetic iron oxide can be dropped and solidify to form a bead (sphere) shape, which is then coated with streptoavidin 8. The size of the magnetic bead 7 is usually in the range of 1 to 5 $\mu$m, preferably 1 $\mu$m. On the other hand, the sample DNA 10 is labeled with biotin 9. By utilizing the specific binding between the streptoavidin 8 and the biotin 9, the sample DNA 10 can be labeled with the magnetic bead 7.

Figure 3:
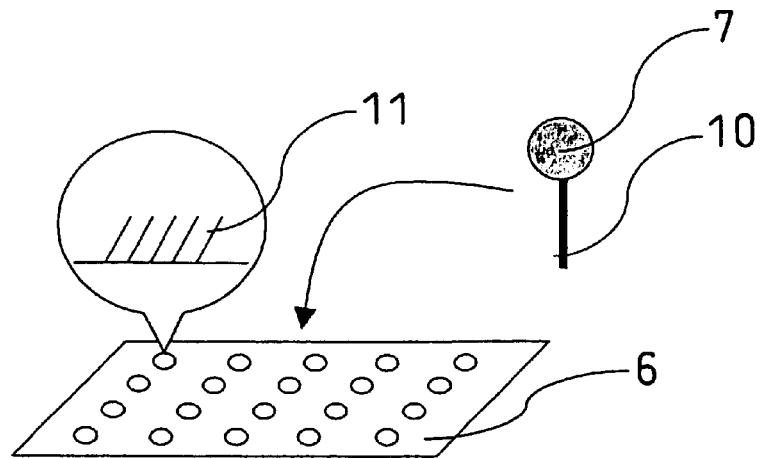
FIGS. 3(a) to 3(c) are views illustrating a method for processing a biochip.
Figure 3:
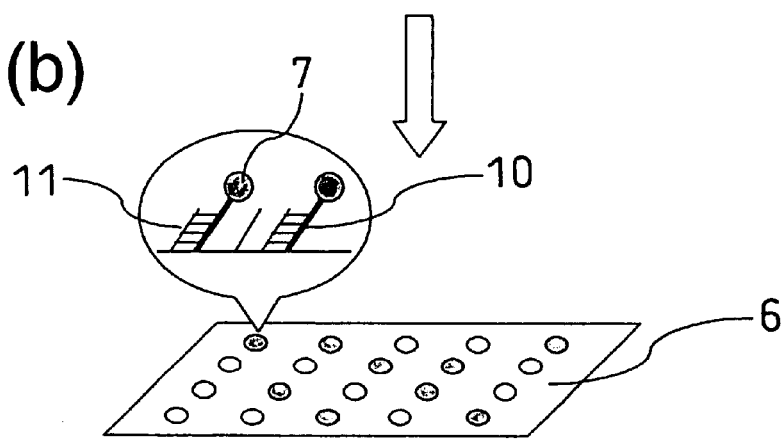
Figure 3:
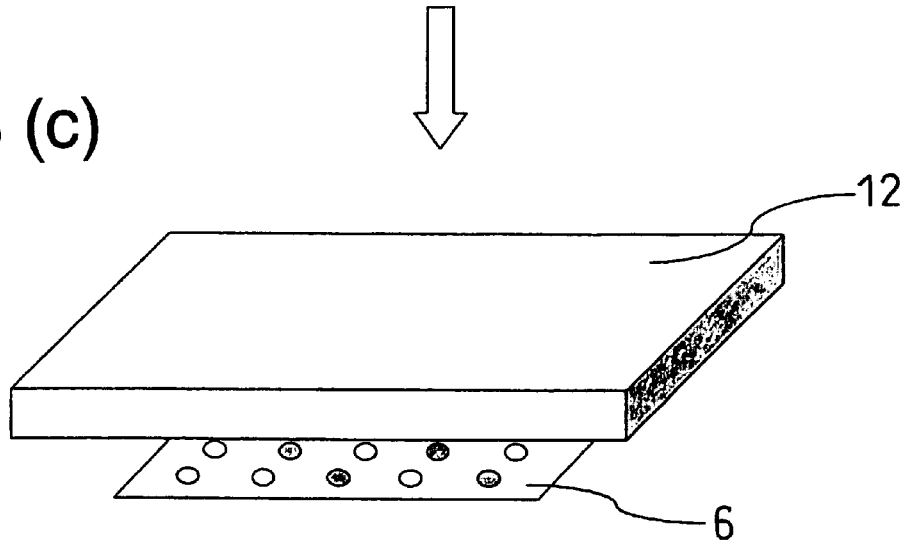

FIGS. 3(a) to (c) are views for illustrating a method for processing a biochip. As shown in FIG. 3(a), labeled sample DNA 10 is reacted with a biochip 6 spotted with probe DNA 11. Then, as shown in FIG. 3(b), the sample DNA 10 hybridizes to spots on the biochip 6 with nucleotide sequences complementary to that of the sample DNA 10. After the hybridization, the biochip 6 is placed in a magnetic field under a magnet 12 as shown in FIG. 3(c) to magnetize the magnetic bead 7. Since the coercive force of the ferromagnetic particulate substance used in the present embodiment is about 320 kAT/m (4000 oersteds), a magnetic field of about three times is applied for magnetization.

Figure 4:
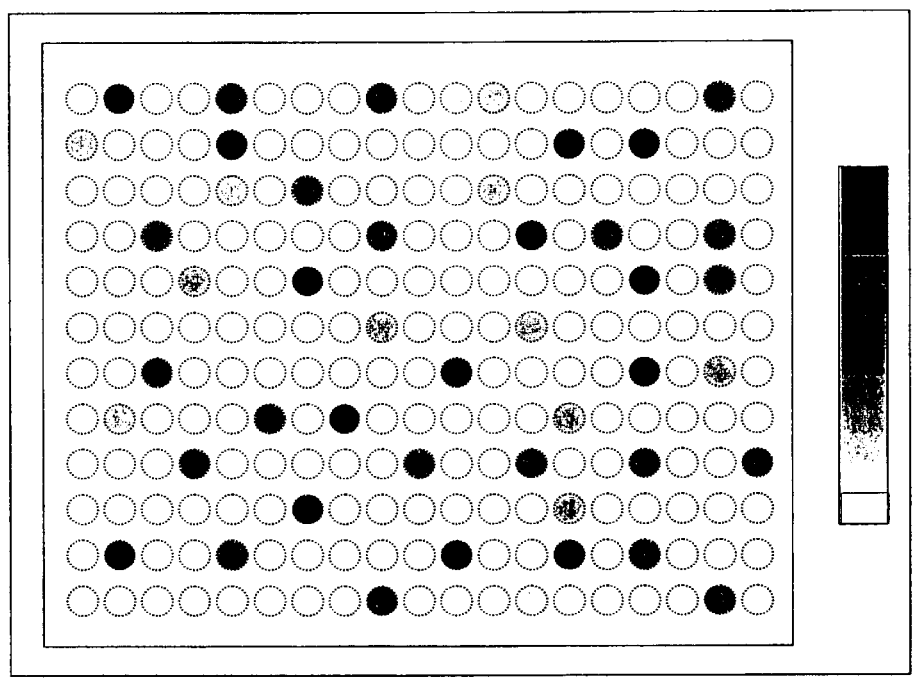
FIG. 4 is a view showing an exemplary result obtained by reading the biochip of the embodiment by a biochip reader of the embodiment.

FIG. 4 is a view showing exemplary results obtained by reading the magnetized biochip 6 with the biochip reader shown in FIG. 1. In FIG. 4, the magnetic field strength of each spot is represented in a gray scale. Darker spot represents a stronger magnetic field where a higher amount of sample DNA is hybridized.

The GMR element used in the device of the present embodiment has a very high detecting sensitivity such that about 30% change of resistance is obtained within a magnetic field range of 0 to 400 oersteds. Therefore, even a single magnetic bead, i.e., a single DNA molecule, can be detected.

Figure 5:
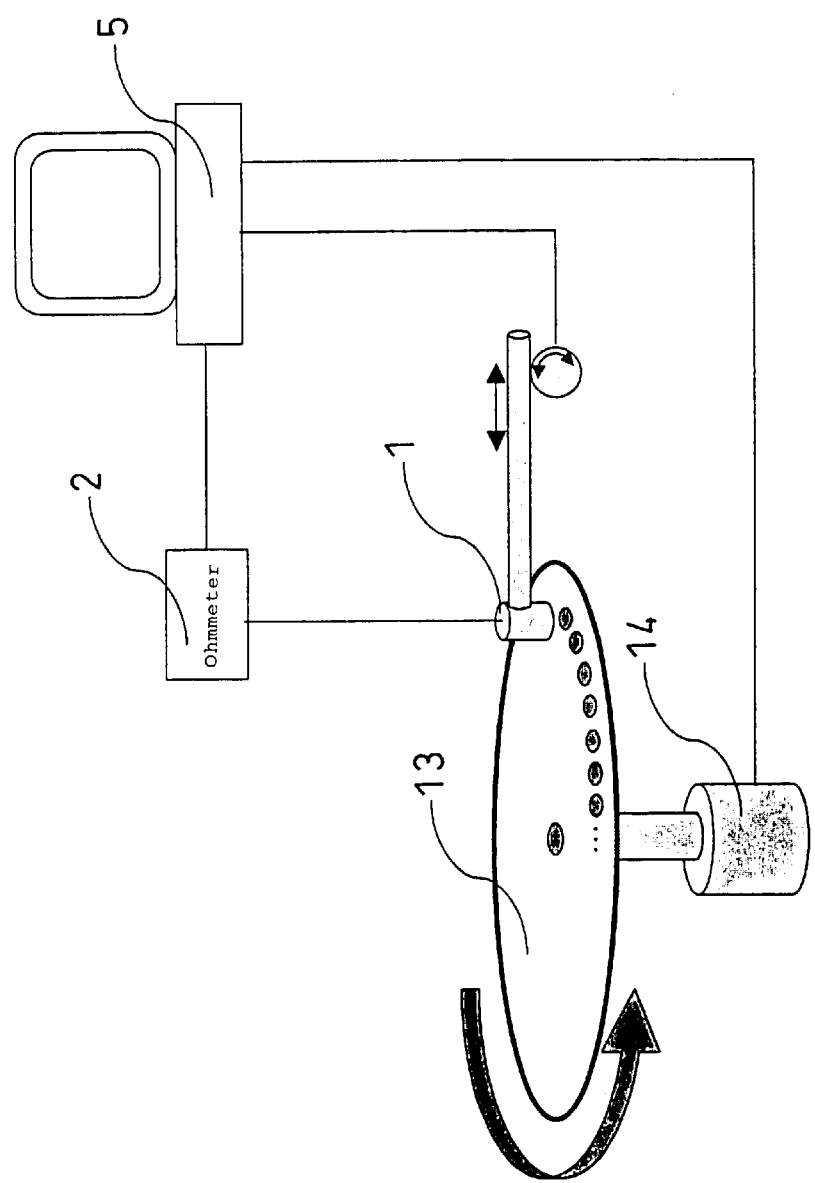
FIG. 5 is a view showing a structure of a biochip reader according to another embodiment of the invention.
Figure 6:
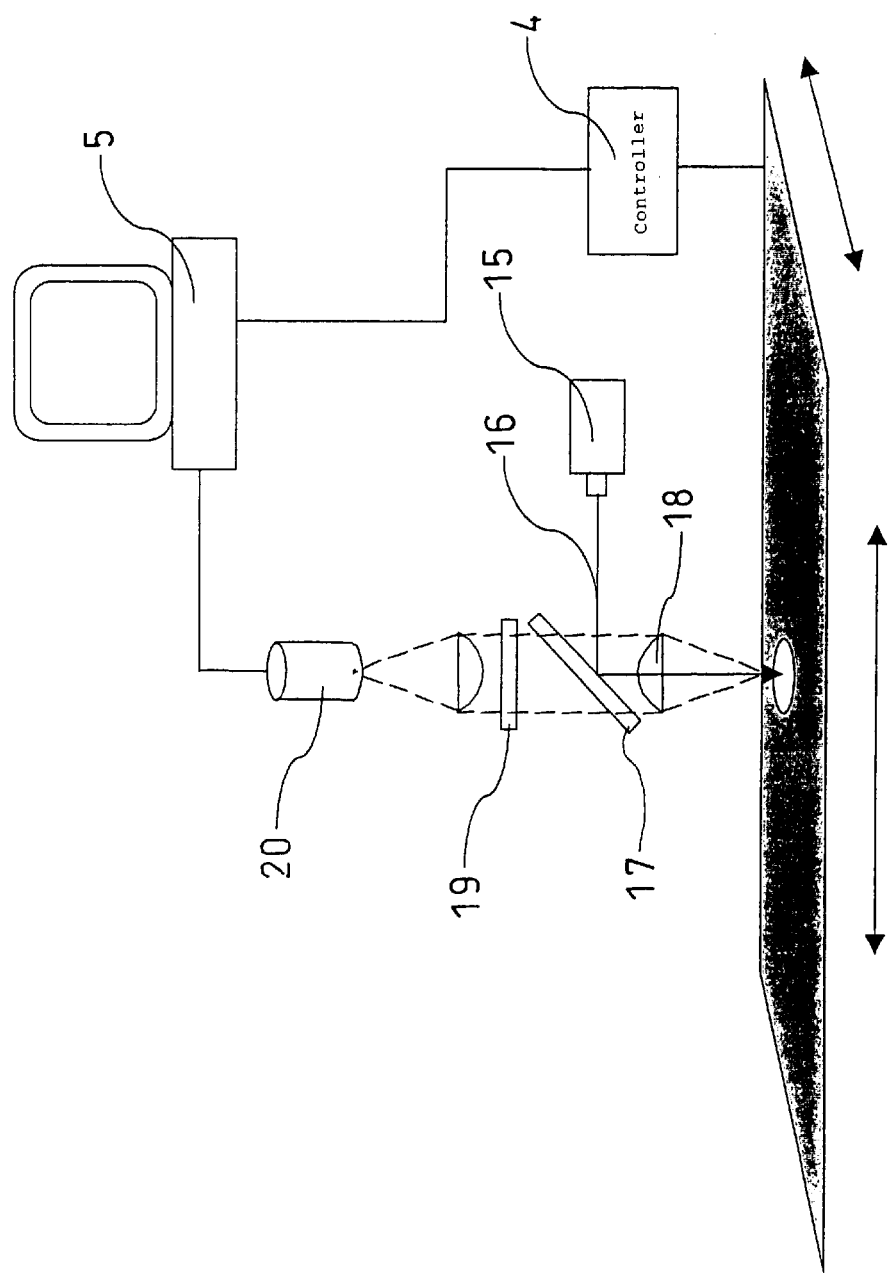
FIG. 6 is a view showing a structure of a conventional biochip reader.

FIG. 5 is a view showing a structure of a biochip reader according to another embodiment of the invention. The reading process is carried out on the same principle as that of the biochip reader shown in FIG. 1 except that a disc-shaped biochip 13 is used, which is rotated while being scanned by a magnetic sensor 1 in a uniaxial direction. In other word, the device reads in the same mechanism as a general hard disk drive. Specifically, the disk-shaped biochip 13 is rotated by a rotary motor 14, and scanned by the magnetic sensor 1 in a direction perpendicular to the rotation direction. Since the same mechanism as that of a general hard disk drive can be employed, highly sensitive and inexpensive device can be obtained.

The present invention is not limited to the above-described embodiments.

Instead of the hard disk drive, the biochip reader may employ a mechanism of a flexible disk drive. In this case, the detachable mechanism of the flexible disk drive can be utilized to attach or remove the biochip.

Instead of collective magnetization with the magnet 12, a writing-only magnetic head of a hard disk drive or the like may be used for magnetization.

Industrial Applicability

As described above, according to the present invention, a high-performance, inexpensive biochip reader can be provided without using an expensive laser or an expensive optical system, by employing a magnetic sensor and a disk driving mechanism generally used in a hard disk drive and the like.

The sensitivity of the magnetic sensor is very high, allowing high-sensitive reading compared to that of a fluorescence reading system. As a result, even a single DNA molecule can be detected.

What is claimed is:

1. A system for reading a biochip using a biochip reader comprising a magnetic sensor for reading the strength of the magnetic field on a plane and a scanning unit for the magnetic sensor and the biochip so that the magnetic sensor scans the biochip relatively in a two-dimensional manner, wherein a sample labeled with a magnetic substance is hybridized to a probe on the biochip, and the magnetic sensor magnetically reads the hybridized sample, and wherein the magnetic substance is a magnetic bead comprising a ferromagnetic substance.

2. The system of claim 1, wherein the magnetic bead is made of polystyrene encapsulating a ferromagnetic iron oxide particulate.

3. The system of claim 1, wherein the sample comprises a binding substance and the magnetic bead is coated with another binding substance specifically binding to the binding substance of the sample, whereby the sample and the magnetic bead are coupled.

4. A system for reading a biochip using a biochip comprising a magnetic sensor for reading the strength of the magnetic field on a plane and a scanning unit for rotating the biochip and the magnetic sensor in a uniaxial direction perpendicular to the rotating direction, wherein a sample labeled with a magnetic substance is hybridized to a probe on the biochip, and the magnetic sensor magnetically reads the hybridized sample, and wherein the magnetic substance is a magnetic bead comprising a ferromagnetic substance.

5. The system of claim 4, wherein the magnetic bead is made of polystyrene encapsulating a ferromagnetic iron oxide particulate.

6. The system of claim 4, wherein the sample comprises a binding substance and the magnetic bead is coated with another binding substance specifically binding to the binding substance of the sample, whereby the sample and the magnetic bead are coupled.

7. The system of claim 6, wherein one of the binding substances comprises streptoavidin and the other binding substance comprises biotin.

8. A system for reading a biochip using a biochip reader comprising a magnetic sensor for reading the strength of the magnetic field on a plane and a scanning unit for the magnetic sensor and the biochip so that the magnetic sensor scans the biochip relatively in a two-dimensional manner, wherein a sample labeled with a magnetic substance is hybridized to a probe on the biochip, and the magnetic sensor magnetically reads the hybridized sample, wherein the sample comprises a binding substance and the magnetic bead is coated with another binding substance specifically binding to the binding substance of the sample, and whereby the sample and the magnetic bead are coupled.

9. A system for reading a biochip using a biochip comprising a magnetic sensor for reading the strength of the magnetic field on a plane and a scanning unit for rotating the biochip and the magnetic sensor in a uniaxial direction perpendicular to the rotating direction, wherein a sample labeled with a magnetic substance is hybridized to a probe on the biochip, and the magnetic sensor magnetically reads the hybridized sample, and wherein the sample comprises a binding substance and the magnetic bead is coated with another binding substance specifically binding to the binding substance of the sample, whereby the sample and the magnetic bead are coupled.

* * * * *